(12) United States Patent
Holladay et al.

(10) Patent No.: US 6,333,189 B1
(45) Date of Patent: *Dec. 25, 2001

(54) METHOD OF MAKING AN ELECTROTRANSPORT DEVICE

(75) Inventors: Leslie A. Holladay, Mountain View, CA (US); Kevin R. Oldenburg, Chaddsford, PA (US)

(73) Assignee: ALZA Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 97 days.

This patent is subject to a terminal disclaimer.

(21) Appl. No.: 08/952,980
(22) PCT Filed: Jun. 6, 1996
(86) PCT No.: PCT/US96/09647
§ 371 Date: Nov. 20, 1997
§ 102(e) Date: Nov. 20, 1997
(87) PCT Pub. No.: WO96/39423
PCT Pub. Date: Dec. 12, 1996

(51) Int. Cl.[7] .......................... C12M 1/00; C12N 13/00; A61N 1/30; A61N 1/04
(52) U.S. Cl. ..................... 435/283.1; 435/285.2; 435/173.6; 604/20; 607/149; 530/350; 530/324; 530/326; 530/327
(58) Field of Search ................ 604/20; 607/149; 530/350, 324, 326, 327; 435/283.1, 285.2, 173.6

(56) References Cited

U.S. PATENT DOCUMENTS

| | | | |
|---|---|---|---|
| H1160 | 4/1993 | Maulding et al. | 604/20 |
| 4,250,878 | 2/1981 | Jacobsen et al. | 128/207 |
| 4,382,529 | 5/1983 | Webster | 604/20 |
| 4,551,271 | 11/1985 | Hochuli | 260/112 |
| 4,631,211 | 12/1986 | Houghten | 428/35 |
| 4,722,726 | 2/1988 | Sanderson et al. | 604/20 |
| 5,080,646 | 1/1992 | Theeuwes et al. | 604/20 |
| 5,169,383 | 12/1992 | Gyory et al. | 604/20 |
| 5,250,023 | 10/1993 | Lee et al. | 604/20 |
| 5,270,170 | 12/1993 | Schatz et al. | 435/7.37 |
| 5,312,326 | 5/1994 | Myers et al. | 604/20 |
| 5,387,189 | 2/1995 | Gyory et al. | 604/20 |
| 5,494,679 | 2/1996 | Sage, Jr. et al. | 424/443 |
| 5,747,453 * | 5/1998 | Holladay | 514/12 |

FOREIGN PATENT DOCUMENTS

| | | | |
|---|---|---|---|
| 278473 | 8/1986 | (EP) | A61K/37/02 |
| WO9212999 | 8/1992 | (WO) | C07K/7/40 |
| WO9213952 | 8/1992 | (WO) | C12N/15/15 |
| WO9325197 | 12/1993 | (WO) | A61K/9/70 |
| WO9325579 | 12/1993 | (WO) | C07K/7/34 |
| WO9511988 | 5/1995 | (WO) | C12P/21/06 |

OTHER PUBLICATIONS

R. Burnette et al., J. Pharm. Sci. (1986) 75:738.
Chien et al. J. Pharm. Sci. (1988) 78:376.

(List continued on next page.)

Primary Examiner—W. Gary Jones
Assistant Examiner—B J Forman
(74) Attorney, Agent, or Firm—Owen J. Bates; D. Byron Miller; Steven F. Stone

(57) ABSTRACT

Method of making an electrotransport device containing an analog of a parent polypeptide having one or more amino acid residues substituted relative to the parent polypeptide with an amino acid residue selected from the group consisting of proline, glycine and asparagine.

5 Claims, 5 Drawing Sheets

OTHER PUBLICATIONS

B.H. Zimm and J.K. Bragg, J. Chem. Phys. (1959) 31:526–535.
S. Lifson and A. Roig, J. Chem. Phys. (1961) 34:1963–1974.
Finkelstein, A.V. Biopolymers (1977) 16:525–529.
Finkelstein et al. Proteins: Structure, Function and Genetics (1991) 10:287–299.
Chou, P.Y. and Fasman, G.D. Ann. Rev. Biochem. (1978) 47:251–276.
M.C. Heit, et al., J. Pharm. Sci., 82, 240–243 (1993).
B.W. Hadzija et al., J. Pharm. Pharmacol., 44, 387–390 (1992).
T.E. Creighton, Proteins: Structures and Molecular Properties (W.H. Freeman and Company, 1993), pp. 255–257.
Qian, H. and Schellmanm J.A., J. Chem. Phys. (1992) 96:3987–3994.
Skolnick, J. and Holtzer, A. Macromolecules (1982) 15:812–821.
Houghten, Proc. Natl. Acad. Sci. USA (1985) 82:5131–5135.
Edge, Nature (1981) 292–756.
Nambair et al., Science (1984) 223:1299.
Jay et al. J. Biol. Chem. (1984) 259:6311.
Beaucage, S.L., et al. Tet. Lett. (1981) 22:1859–1862.
Matteucci, M.D., et al., J. Am. Chem. Soc. (1981) 103:3185–3191.
Zoller and Smith, Methods Enzymol. (1983) 100:468.
Dalbie–McFarland et al., Proc. Natl. Acad. Sci USA (1982) 79:6409.
Maragnore et al. Biochem. (1990) 29:7095–7101.
Sueki et al., Macromolecules (1984) 17:148–155.
Maraganore et al., Thromb. Haemostasis (1991) 65:830.
Bode et al., EMBO J. (1989) 8:3467–3475.
Pharmacokinetics, M. Gibaldi, 2d ed. Marcel Dekker (1982), pp. 1–5 and 319–322.
Witting et al., Biochem. J. (1992) 287:663–664.
Derynck et al., Cell (1984) 38:287–297.
Miozzari and Yanofsky J., Bacteriol. (1978) 133:1457–1466.

* cited by examiner

Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Leu-Gln-Asp-Val-His-Asn-Phe

FIG. 1A  (SEQ ID NO: 6)

Ser-Val-Ser-Glu-Ile-Gln-Leu-Leu-His-Asn-Leu-Gly-Lys-His-Arg-Asn-Ser-Leu-Arg-Arg-Val-Arg-Trp-Leu-Arg-Lys-Leu-Lys-Asp-Val-His-Asn-Tyr-HSL

FIG. 1B  (SEQ ID NO: 7)

Ser-Val-Ser-Glu-Ile-Gln-Leu-Leu-His-Asn-Ser-Gly-Lys-His-Arg-Asn-Ser-Ser-Arg-Arg-Val-Arg-Trp-Ser-Arg-Lys-Leu-Lys-Asp-Val-His-Asn-Ser-HSL

FIG. 1C  (SEQ ID NO: 8)

Ser-Val-Ser-Glu-Ile-Gln-Leu-Met-His-Asn-Leu-Gly-Lys-His-Leu-Asn-Ser-Met-Glu-Arg-Pro-Glu-Trp-Leu-Arg-Lys-Leu-Lys-Pro-Gln-Asp-Val-His-Asn-Phe

FIG. 1D  (SEQ ID NO: 9)

(D-Cha)-Ala-Arg-Ala-Ala-Ala-Ala-Asn-Ala-Asp-Phe-Glu-Glu-Ile-Ala-Glu-Glu-Tyr-Leu

FIG. 2A (SEQ ID NO: 10)

(D-Phe)-Pro-Arg-Pro-Gly-Gly-Gly-Gly-Asn-Gly-Asp-Phe-Glu-Glu-Ile-Pro-Glu-Glu-Tyr-Leu

FIG. 2B (SEQ ID NO: 11)

(D-Cha)-Pro-Arg-Pro-Gly-Gly-Gly-Gly-Asn-Gly-Asp-Phe-Glu-Glu-Ile-Pro-Glu-Glu-Tyr-Leu

FIG. 2C (SEQ ID NO: 12)

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 80 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GCTCGGGCTA GCTAACTAAT GGAGGATACA TAAATGAAAG CTATCTTCGT TCTGAAAGGT     60

TCCCTGGACC GTGACCCGGA                                                 80
```

(2) INFORMATION FOR SEQ ID NO:2:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
GGACGGAAGC TTTTATTAAT GGTGATGGTG GTGGTGGGAG ATCTGGTTGA TCATGTCGAC    60

GAATTCCGGG TCACGGTCCA                                                80
```

(2) INFORMATION FOR SEQ ID NO:3:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 7..138

(ix) FEATURE:
        (A) NAME/KEY: mat_peptide
        (B) LOCATION: 25

(xi) SEQUENCE DESCRIPTION: SEQ ID NO:3:

```
GGCTGG GTC GAC ATG ATC AAC ATG TCC GTT TCC GAA ATC CAG CTG CTG      48
       Val Asp Met Ile Asn Met Ser Val Ser Glu Ile Gln Leu Leu
        -6  -5                   1               5

CAC AAC CTG GGT AAA CAC CTG AAC TCC CTC GAG CGT GTT GAA TGG CTG     96
His Asn Leu Gly Lys His Leu Asn Ser Leu Glu Arg Val Glu Trp Leu
         10              15                  20

CGT AAA AAA CTG CAG GAC GTC CAC AAC TAC ATG CAG ATC TCC             138
Arg Lys Lys Leu Gln Asp Val His Asn Tyr Met Gln Ile Ser
 25              30                  35

CTC                                                                  141
```

(2) INFORMATION FOR SEQ ID NO:4:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:4:

```
Val Asp Met Ile Asn Met Ser Val Ser Glu Ile Gln Leu Leu His Asn
 -6  -5                   1               5                  10

Leu Gly Lys His Leu Asn Ser Leu Glu Arg Val Glu Trp Leu Arg Lys
                 15                  20                  25

Lys Leu Gln Asp Val His Asn Tyr Met Gln Ile Ser
                 30                  35
```

(2) INFORMATION FOR SEQ ID NO:5:

(i) SEQUENCE CHARACTERISTICS:
        (A) LENGTH: 141 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GAGGGAGATC TGCATGTAGT TGTGGACGTC CTGCAGTTTT TTACGCAGCC ATTCAACACG      60

CTCGAGGGAG TTCAGGTGTT TACCCAGGTT GTGCAGCAGC TGGATTTCGG AAACGGACAT     120

GTTGATCATG TCGACCCAGC C                                               141

(2) INFORMATION FOR SEQ ID NO:6:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Ser Val Ser Glu Ile Gln Leu Met His Asn Leu Gly Lys His Leu Asn
1               5                   10                  15
Ser Met Glu Arg Val Glu Trp Leu Arg Lys Lys Leu Gln Asp Val His
            20                  25                  30
Asn Phe (2) INFORMATION FOR SEQ ID NO:7:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: misc_feature
        (B) LOCATION: 35
        (D) OTHER INFORMATION: /note= "'Xaa' represents
            Homoserine/Homoserine Lactone"

(xi) SEQUENCE DESCRIPTION: SEQ ID NO:7:

Ser Val Ser Glu Ile Gln Leu Leu His Asn Leu Gly Lys His Arg Asn
1               5                   10                  15
Ser Leu Arg Arg Val Arg Trp Leu Arg Lys Lys Leu Lys Asp Val His
            20                  25                  30
Asn Tyr Xaa
        35

(2) INFORMATION FOR SEQ ID NO:8:

(i) SEQUENCE CHARACTERISTICS:
        (A) LENGTH: 35 amino acids
        (B) TYPE: amino acid
        (C) STRANDEDNESS: single
        (D) TOPOLOGY: linear (ix) FEATURE:
        (A) NAME/KEY: Misc_feature
        (B) LOCATION: 35
        (D) OTHER INFORMATION: /note= "'Xaa' represents
            Homoserine/Homoserine Lactone"

(ii) MOLECULE TYPE: protein (xi) SEQUENCE DESCRIPTION: SEQ ID NO:8:

Ser Val Ser Glu Ile Gln Leu Leu His Asn Ser Gly Lys His Arg Asn
1               5                   10                  15

Ser Ser Arg Arg Ser Arg Trp Ser Arg Lys Lys Ser Lys Asp Val His
                20                  25                  30

Asn Ser Xaa
        35

(2) INFORMATION FOR SEQ ID NO:9:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Ser Val Ser Glu Ile Gln Leu Met His Asn Leu Gly Lys His Leu Asn
1               5                   10                  15

Ser Met Glu Arg Pro Glu Trp Leu Arg Lys Lys Pro Gln Asp Val His
                20                  25                  30

Asn Phe (2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ix) FEATURE:
        (A) NAME/KEY: Misc_feature
        (B) LOCATION: 1
        (D) OTHER INFORMATION: /note= "'Xaa' represents
            D-Cyclohexylalanine"

(ii) MOLECULE TYPE: protein (xi) SEQUENCE DESCRIPTION: SEQ ID NO:10:

Xaa Ala Arg Ala Ala Ala Ala Asn Ala Asp Phe Glu Glu Ile Ala
1               5                   10                  15

Glu Glu Tyr Leu
        20

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ix) FEATURE:
        (A) NAME/KEY: Misc_feature
        (B) LOCATION: 1
        (D) OTHER INFORMATION: /note= "'Xaa' represents
            D-Phenylalanine"

(ii) MOLECULE TYPE: protein (xi) SEQUENCE DESCRIPTION: SEQ ID NO:11:

Xaa Pro Arg Pro Gly Gly Gly Gly Asn Gly Asp Phe Glu Glu Ile Pro
1               5                   10                  15

```
Glu Glu Tyr Leu
        20

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ix) FEATURE:
        (A) NAME/KEY: Misc_feature
        (B) LOCATION: 1
        (D) OTHER INFORMATION: /note= "'Xaa' represents
            D-Cyclohexylalanine"

(ii) MOLECULE TYPE: protein (xi) SEQUENCE DESCRIPTION: SEQ ID NO:12:

Xaa Pro Arg Pro Gly Gly Gly Asn Gly Asp Phe Glu Glu Ile Pro
1               5                   10                  15

Glu Glu Tyr Leu
        20
```

METHOD OF MAKING AN ELECTROTRANSPORT DEVICE

This application is a 371 of PCT/US96/09647 filed Jun. 9, 1996.

TECHNICAL FIELD

The invention relates generally to electrotransport drug delivery. More particularly, the invention relates to a method for increasing electrotransport flux of a polypeptide by reducing the potential of the polypeptide for forming α-helical or β-sheet segments. The invention also pertains to molecules which have been so modified.

BACKGROUND ART

Transdermal (ie, through the skin) delivery of therapeutic agents affords a comfortable, convenient and noninvasive technique for administering drugs. The method provides several advantages over conventional modes of drug delivery. For example, variable rates of absorption and (eg, hepatic) metabolism encountered in oral treatment are avoided, and other inherent inconveniences—eg, gastrointestinal irritation and the like—are eliminated. Transdermal delivery also allows a high degree of control over blood concentrations of a particular drug and is an especially attractive administration route for drugs with narrow therapeutic indexes, short half-lives and potent activities.

Transdermal delivery can be either passive or active. Many drugs are not suitable for passive transdermal drug delivery because of their size, ionic charge characteristics and hydrophobicity. One method of overcoming this limitation is the use of low levels of electric current to actively transport drugs into the body through intact skin. This technique is known as "electrotransport" or "iontophoretic" drug delivery. The technique provides a more controllable process than passive transdermal drug delivery since the amplitude, timing and polarity of the applied electric current is easily regulated using standard electrical components. In this regard, electrotransport drug flux can be from 50% to several orders of magnitude greater than passive transdermal flux of the same drug.

Electrotransport devices generally employ at least two electrodes. Both of these electrodes are positioned in intimate electrical contact with some portion of the skin of the body. One electrode, called the active or donor electrode, is the electrode from which the therapeutic agent is delivered into the body. The other electrode, called the counter or return electrode, serves to close the electrical circuit through the body. In conjunction with the patient's skin, the circuit is completed by connection of the electrodes to a source of electrical energy, eg, a battery, and usually to circuitry capable of controlling current passing through the device.

Depending upon the electrical charge of the species to be delivered transdermally, either the anode or cathode may be the active or donor electrode. In this regard, if the ionic substance to be driven into the body is positively charged, then the positive electrode (the anode) will be the active electrode and the negative electrode (the cathode) will serve as the counter electrode, completing the circuit. On the other hand, if the ionic substance to be delivered is negatively charged, then the cathodic electrode will be the active electrode and the anodic electrode will be the counter electrode. Alternatively, both the anode and the cathode may be used to deliver drugs of appropriate charge into the body. In this case, both electrodes are considered to be active or donor electrodes. In other words, the anodic electrode can deliver positively charged agents into the body while the cathodic electrode can deliver negatively charged agents into the body.

Existing electrotransport devices additionally require a reservoir or source of the therapeutic agent that is to be delivered into the body. Such drug reservoirs are connected to the anode or the cathode of the electrotransport device to provide a fixed or renewable source of one or more desired species or agents. Examples of reservoirs and sources include a pouch as described in U.S. Pat. No. 4,250,878 to Jacobsen; a pre-formed gel body as disclosed in U.S. Pat. No. 4,382,529 to Webster; and a glass or plastic container holding a liquid solution of the drug, as disclosed in the figures of U.S. Pat. No. 4,722,726 to Sanderson et al.

Of particular interest herein is the transdermal electrotransport delivery of peptides, polypeptides, and proteins because of the problems encountered with more common drug administration routes such as oral delivery. Polypeptide and protein molecules are highly susceptible to degradation by proteolytic enzymes in the gastrointestinal tract and are subjected to an extensive hepatic metabolism when taken orally. Polypeptides and proteins usually require parenteral administration to achieve therapeutic levels in the patient's blood. The most conventional parenteral administration techniques are hypodermic injections and intravenous administration. Polypeptides and proteins are, however, inherently short acting in their biological activity, requiring frequent injections, often several times a day, to maintain the therapeutically effective levels needed. Patients frequently find this treatment regimen to be inconvenient, painful and with an attendant risk of, eg, infection.

Much effort has been expended to find other routes (other than parenteral injections) for effective administration of pharmaceutical polypeptides and proteins. Administration routes with fewer side effects as well as better patient compliance have been of particular interest. Such alternative routes have generally included "shielded" oral administration wherein the polypeptide/protein is released from a capsule or other container after passing through the low pH environment of the stomach, delivery through the mucosal tissues, eg, the mucosal tissues of the lung with inhalers or the nasal mucosal tissues with nasal sprays, and implantable pumps. Unfortunately, these alternative routes of polypeptide/protein delivery have met with only limited success.

Transdermal electrotransport delivery of polypeptides and proteins has also encountered technical difficulties. For example, water is the preferred liquid solvent for forming the solution of the drug being delivered by electrotransport due to its excellent biocompatibility. The skin contains proteolytic enzymes which may degrade the polypeptide/protein as it is delivered transdermally. In addition, certain polypeptides/proteins, particularly those that are not native to the animal being treated, may cause skin reactions, eg, sensitization or irritation.

A number of investigators have disclosed electrotransport delivery of polypeptides and proteins. An early study by R. Bumette et al. *J. Pharm. Sci.* (1986) 75:738, involved in vitro skin permeation of thyrotropin releasing hormone, a small tripeptide molecule. The electrotransport flux was found to be higher than passive diffusional flux. Chien et al. *J. Pharm. Sci.* (1988) 78:376, in both in vitro and in vivo studies, showed that transdermal delivery of vasopressin and insulin via electrotransport was possible. See, also, Maulding et al., U.S. Statutory Invention Registration No. H1160, which discloses electrotransport delivery of calcitonin in minipigs.

Several approaches (other than simply increasing the applied levels of electrotransport current) have been used to enhance transdermal electrotransport flux of polypeptide and protein drugs. One approach involves the use of flux enhancers such as ionic surfactants. See, eg, U.S. Pat. No. 4,722,726 to Sanderson et al. Another approach uses cosolvents other than just water to enhance electrotransport flux. See, eg, European Patent Application 278,473. Yet another approach involves mechanically disrupting the outer layer (ie, the stratum corneum) of the skin prior to electrotransport delivery therethrough. See, eg, U.S. Pat. No. 5,250,023 to Lee et al.

Further approaches to enhancing transdermal electrotransport drug flux involve creating a prodrug or an analog of the drug of interest and electrotransporting the prodrug or modified analog. For example, WO 92/12999 discloses delivery of insulin as an insulin analog having a reduced tendency to self-associate (apparently associated forms of insulin present in conventional pharmaceutical compositions reduce transdermal delivery of the insulin). The analogs are created by substituting aspartic acid (Asp) or glutamic acid (Glu) for other amino acid residues at selected positions along the insulin polypeptide chain. WO 93/25197 discloses delivery of both peptide and non-peptide drugs as pharmaceutical agent-modifier complexes or prodrugs wherein a chemical modifier (eg, a charged moiety) is covalently bonded to the parent pharmaceutical agent. The covalent bond is broken after the agent is delivered into the body, thereby releasing the parent agent.

Despite the above approaches, some polypeptides still exhibit poor transdermal electrotransport flux. In particular, peptide hydrophobicity is known to negatively impact electrotransport flux in vitro. Various parameters contribute to hydrophobicity, including the primary structure of a protein, ie, the amino acid sequence of the molecule, as well as the secondary structure of the protein, namely, the regular, recurring arrangement of the polypeptide chain along three dimensions. Such conformation can take the form of helical structures, such as an α-helix, or a more extended, zigzag conformation, known as the β-conformation.

The α-helix has approximately 3.6 residues per turn of the helix. The R groups of the amino acids extend outward from the helix and intrachain hydrogen bonds are formed between the backbone carbonyl oxygen of each residue and backbone hydrogen atom attached to the electronegative nitrogen of the fourth residue along the chain. The basic unit of the β-conformation is the β-strand which exists as a less tightly coiled helix, with 2.0 residues per turn. The β-strand conformation is only stable when incorporated into a β-sheet, where hydrogen bonds with close to optimal geometry are formed between the peptide groups on adjacent β-strands; the dipole moments of the strands are also aligned favorably. Side chains from adjacent residues of the same strand protrude from opposite sides of the sheet and do not interact with each other, but have significant interactions with their backbone and with the side chains of neighboring strands. For a general description of α-helices and β-sheets, see, eg, T. E. Creighton, *Proteins: Structures and Molecular Properties* (W. H. Freeman and Company, 1993); and A. L. Lehninger, *Biochemistry* (Worth Publishers, Inc., 1975)

The Zimm-Bragg parameters, s and σ (B. H. Zimm and J. K Bragg *J. Chem. Phys.* (1959) 31:526–535), and Lifson-Roig equations (S. Lifson and A Roig *J. Chem. Phys.* (1961) 34:1963–1974) are conventionally used to determine the stability of a helical segment in a given polypeptide. S represents the helix-coil stability constant and a is the nucleation factor. Based on these parameters, the likelihood of certain regions of polypeptide molecules to form α-helices and β-sheets can be predicted using various calculations and computer programs. See, eg, Finkelstein, A. V. Program "ALB" for protein and polypeptide secondary structure calculation and prediction (1983). Deposited at the Brookhaven Protein Data Bank, Upton, N.Y. and at the EMBL, Heidelberg, Germany; Finkelstein, A. V. Biopolymers (1977) 16:525–529; Finkelstein et al. *Proteins: Structure, Function and Genetics* (1991) 10:287–299. Furthermore, Chou-Fasman probabilities (Chou, P. Y. and Fasman, G. D. *Ann. Rev. Biochem.* (1978) 47:251–276) have been used to assess the propensity of a particular amino acid residue to favor or disfavor α-helical and β-sheet formation.

However, these principles have not been previously applied to alter the hydrophobic properties of a given polypeptide in order to increase the electrotransport flux thereof.

DISCLOSURE OF THE INVENTION

In accordance with the present invention, the electrotransport flux of a given polypeptide is enhanced by disrupting its secondary structure. In particular, amino acid residues known to stabilize α-helical and β-sheet segments can be replaced with destabilizing residues and known helix breakers. In this way, the flux of the polypeptide through a body surface (eg, the skin) may be increased, thereby allowing electrotransport delivery of a wider range of polypeptide drugs at therapeutically effective rates.

Accordingly, in one embodiment, the invention relates to a method of making an analog of a parent polypeptide having an α-helical and/or β-sheet segment, the analog exhibiting better/enhanced electrotransport- ability through a body surface, the method comprising substituting one or more amino acid residues of the parent polypeptide in the analog polypeptide, to disrupt one or more α-helical and/or β-sheet segments of the parent polypeptide. The analog polypeptide exhibits enhanced electrotransport as compared to the parent polypeptide.

In an additional embodiment, the invention pertains to a method for delivering a polypeptide agent through a body surface. The method comprises (a) providing an analog of a parent polypeptide wherein the parent polypeptide comprises an α-helical and/or β-sheet segment, the analog polypeptide having one or more amino acid residues substituted relative to the parent polypeptide; and (b) delivering the analog polypeptide through the body surface by electrotransport.

In particularly preferred embodiments, the disrupting is done by substituting one or more amino acid residues of the parent polypeptide, with one or more amino acid residues having a lower Pα or Pβ value than the parent amino acid residue.

In another embodiment, the invention is directed to a parathyroid hormone (PTH) analog comprising the amino acid sequence depicted in FIG. 1B (SEQ ID NO:7).

In yet another embodiment, the invention is directed to a parathyroid hormone (PTH) analog comprising the amino acid sequence depicted in FIG. 1C (SEQ ID NO:8).

These and other embodiments of the subject invention will readily occur to those of skill in the art in light of the disclosure herein.

BRIEF DESCRIPTION OF THE DRAWINGS

FIG. 1 shows the amino acid sequence of various parathyroid hormone ("PTH") molecules used to exemplify the invention.

FIG. 1A (SEQ ID NO:6) shows the amino acid sequence of the wild-type, parent PTH polypeptide.

FIG. 1B (SEQ ID NO:7) shows the amino acid sequence of PTH analog 1 (1–35).

FIG. 1C (SEQ ID NO:8) shows the amino acid sequence of PTH analog 2 (1–35).

FIG. 1D (SEQ ID NO:9) shows the amino acid sequence of PTH analog 3. HSL denotes homoserine/homoserine lactone. The underlined residues in FIGS. 1B (SEQ ID NO:7), 1C (SEQ ID NO:8) and 1D (SEQ ID NO:9) indicate positions of substitution.

FIG. 2 (SEQ ID NOS:10, 11, 12) shows the amino acid sequences of various hirudin derivative polypeptides used to exemplify the invention.

FIG. 2A (SEQ ID NO:10) shows the amino acid sequence of a hirulog parent polypeptide.

FIG. 2B (SEQ ID NO:11) shows the amino acid sequence of hirulog-1. FIG. 2C (SEQ ID NO:12) shows the sequence of hirulog-B2.

Figure 3:
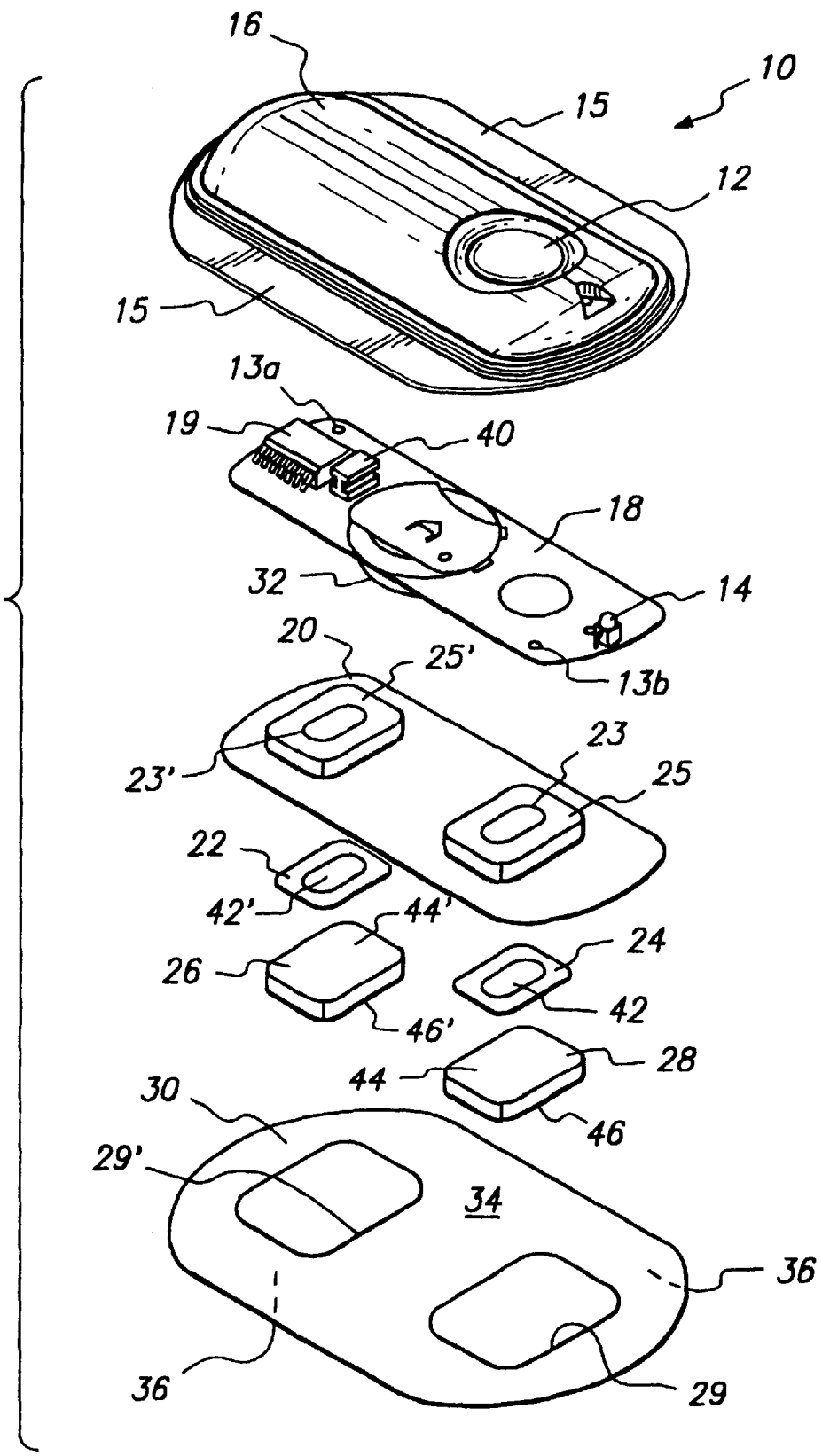

FIG. 3 is a schematic view of a representative electrotransport drug delivery device which can be used with the present invention.

Figure 4:
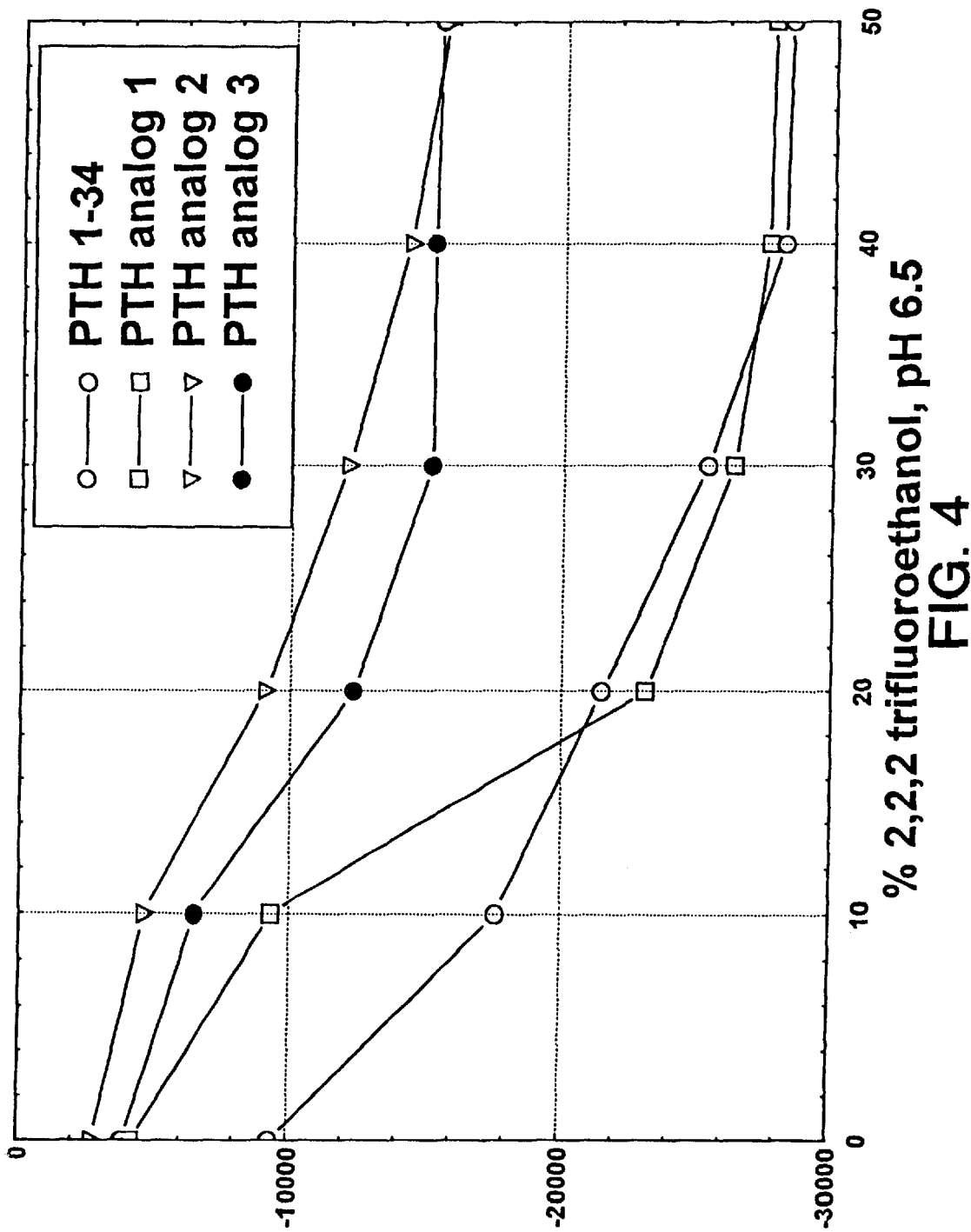

FIG. 4 is a graph of mean residue ellipticity of several parathyroid hormone analogs versus concentration of trifluoroethanol.

Figure 5:
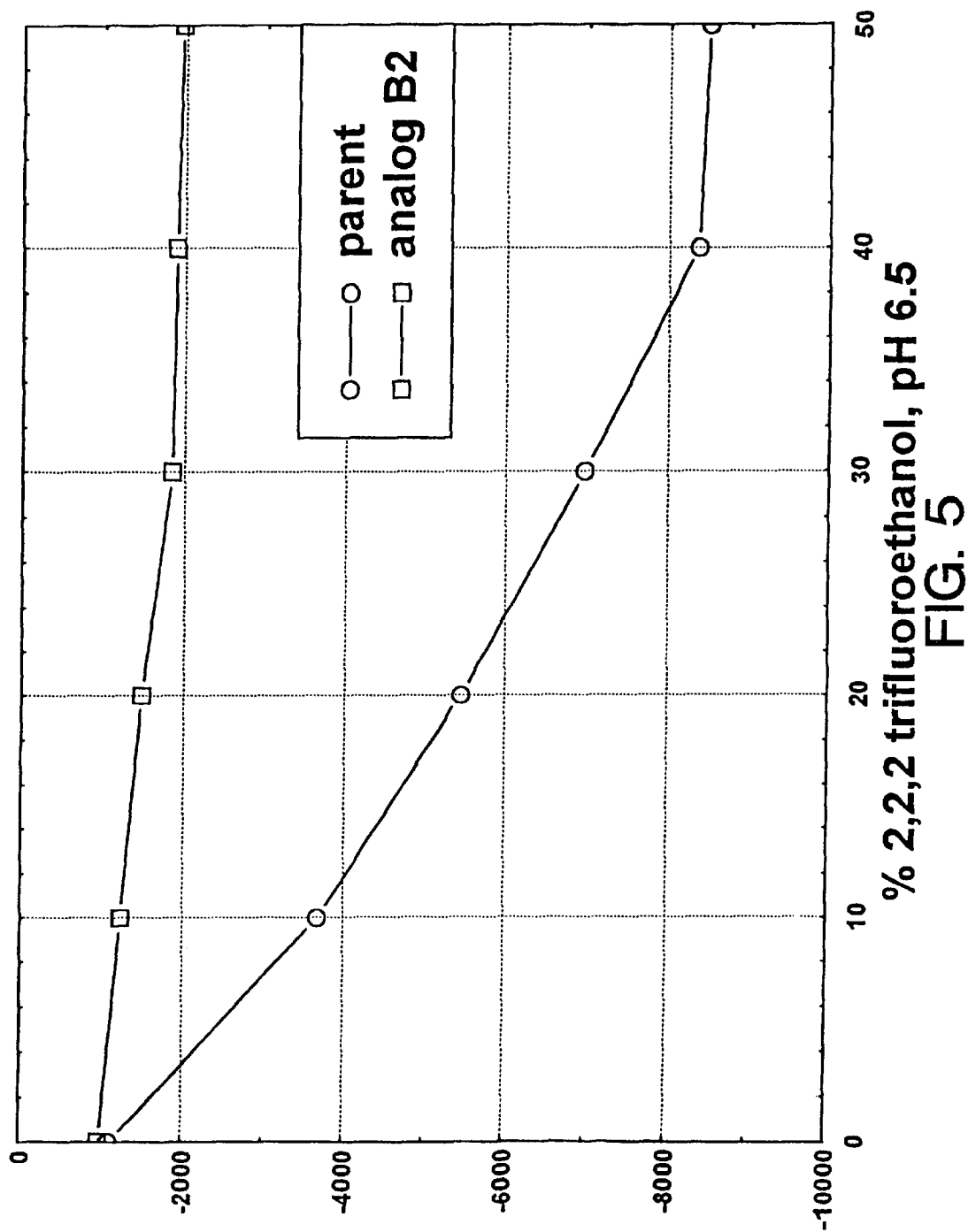

FIG. 5 is a graph of mean residue ellipticity of two hirudin derivative polypeptides versus concentration of trifluoroethanol.

DETAILED DESCRIPTION OF THE INVENTION

The practice of the present invention will employ, unless otherwise indicated, conventional methods of protein chemistry, electrochemistry, molecular biology and recombinant DNA techniques within the skill of the art. Such techniques are explained fully in the literature. See, eg, T. E. Creighton, *Proteins: Structures and Molecular Properties* (W.H. Freeman and Company, 1993); A. L. Lehninger, *Biochemistry* (Worth Publishers, Inc., 1975); J. S. Newman, *Electrochemical Systems* (Prentice Hall, 1973); A. J. Bard and L. R. Faulkner, *Electrochemical Methods, Fundamentals and Applications* (John Wiley & Sons, 1980); Sambrook, et al., *Molecular Cloning: A Laboratory Manual* (Cold Spring Harbor Laboratory, 1989).

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

I. Definitions

In describing the present invention, the following terms will be employed, and are intended to be defined as indicated below.

Herein the terms "electrotransport", "iontophoresis" and "iontophoretic" are used to refer to the delivery through a body surface (eg, skin) of one or more pharmaceutically active polypeptide agents by means of an applied electromotive force to an agent-containing reservoir. The agent may be delivered by electromigration, electroporation, electroosmosis or any combination thereof. Electroosmosis has also been referred to as electrohydrokinesis, electroconvection, and electrically induced osmosis. In general, electroosmosis of a species into a tissue results from the migration of solvent in which the species is contained, as a result of the application of electromotive force to the therapeutic species reservoir, ie, solvent flow induced by electromigration of other ionic species. During the electrotransport process, certain modifications or alterations of the skin may occur such as the formation of transiently existing pores in the skin, also referred to as "electroporation". Any electrically assisted transport of species enhanced by modifications or alterations to the body surface (eg, formation of pores in the skin) are also included in the term "electrotransport" as used herein. Thus, as used herein, the terms "electrotransport", "iontophoresis" and "iontophoretic" refer to (1) the delivery of charged agents by electromigration, (2) the delivery of uncharged agents by the process of electroosmosis, (3) the delivery of charged or uncharged agents by electroporation, (4) the delivery of charged agents by the combined processes of electromigration and electroosmosis, and/or (5) the delivery of a mixture of charged and uncharged agents by the combined processes of electromigration and electroosmosis.

The terms "polypeptide," "polypeptide agent" and "polypeptide drug" are used interchangeably herein to denote any bioactive polymer of amino acid residues. The terms encompass peptides, oligopeptides, dimers, multimers, and the like. Such polypeptides can be derived from natural sources or can be synthesized or recombinantly produced. The terms also include postexpression modifications of the polypeptide, for example, glycosylation, acetylation, phosphorylation, etc.

A polypeptide drug or agent as defined herein is generally made up of the 20 natural amino acids Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-methylenecyclopropyl) glycine, S-methylcysteine, S-(prop-I-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents which will find use in the present invention are set forth below.

By "parent" polypeptide, polypeptide agent or polypeptide drug, is meant a polypeptide as defined above, which includes α-helical or β-sheet segments which can be modified such that the electrotransport flux of the polypeptide is enhanced. In particular, a parent polypeptide will generally include from about 10 to about 50 amino acid residues, more preferably from about 10 to about 40 amino acid residues. Furthermore, the parent polypeptide will be one which is not prone to adopt a stable tertiary folded structure in solution, eg, as a result of a high concentration of Cys residues. The parent polypeptide can be a naturally occurring polypeptide or may itself have structural differences from a naturally occurring polypeptide such as is amino acid substitutions, deletions or additions, as well as post-translational modifications as described above.

By polypeptide "analog" is meant a polypeptide as defined above, which results from the modification of the secondary structure of the parent polypeptide. In this regard, the analog differs from the parent by way of substitution of one or more amino acid residues such that one or more α-helical and/or β-helical segments present in the parent molecule are disrupted. Appropriate amino acid substitutions are discussed more fully below. The analog can also contain additional modifications that do not affect secondary structure, such as additional amino acid substitutions, deletions or additions, or post-translational modifications as described above. The analog can also exist in neutral or salt forms, eg, acid addition salts (formed with the free amino groups of the analog polypeptides) and which are formed with inorganic acids such as, for example, hydrochloric or phosphoric acids, or such organic acids as acetic, succinic, maleic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, and the like. The polypeptide analog will have at least some of the bioactivity of the parent polypeptide, and more preferably will have the same or greater bioactivity of the parent molecule.

By "enhancing the electrotransport" of a polypeptide is meant increasing the electrotransport flux of the polypeptide through the body surface (eg, the skin or mucosa) as compared to the parent polypeptide. Transdermal electrotransport flux can be determined using a number of in vivo or in vitro methods well known in the art. In vitro methods include clamping a piece of skin of an appropriate animal (eg, human cadaver skin) between the donor and receptor compartments of an electrotransport flux cell, with the stratum corneum side of the skin piece facing the donor compartment. A liquid solution or gel containing the drug to be delivered is placed in contact with the stratum corneum, and electric current is applied to electrodes, one electrode in each compartment. The transdermal flux is calculated by sampling the amount of drug in the receptor compartment. Two successful models used to optimize transdermal electrotransport drug delivery are the isolated pig skin flap model of Riviere, M. C. Heit, et al, J. Pharm. Sci, 82, 240–243 (1993), and the use of isolated hairless skin from hairless rodents or guinea pigs, for example. See B. W. Hadzija et al, J. Pharm. Pharmacol., 44, 387–390 (1992).

II. Modes of Carrying Out the Invention

The present invention concerns substituting amino acids which disrupt α-helical and β-sheet segments of a polypeptide molecule to enhance the electrotransport flux of that molecule as compared to the flux of the parent polypeptide. The method therefore permits electrotransport of a large number of substances that would not otherwise be amenable to such delivery. Without being bound by a particular theory, it appears that such secondary changes decrease the tendency of hydrophobic side chains of amino acid residues such as Leu, Phe and Trp, to become spatially clustered. Thus, the ability of the molecule to bind to hydrophobic areas in the skin during electrotransport is reduced, thereby facilitating passage of the polypeptide through the skin.

The present invention has been exemplified using a parathyroid hormone (PTH) molecule and a hirudin derivative as the parent compounds. PTH is a peptide hormone which regulates homeostatic control of calcium and phosphate metabolism and has been used to treat osteoporosis. Wild-type PTH is shown in FIG. 1A (SEQ ID NO:6). The molecule has 34 amino acid residues and a molecular weight of approximately 4000 daltons. As shown herein, the is molecule has a very large tendency to adopt the α-helical formation.

Hirulog is a hirudin-based synthetic peptide anticoagulant which effectively inhibits both free and fibrin-bound thrombin. Hirulog has been shown to inhibit post-operative venous thrombosis in patients undergoing orthopedic surgery. The sequence of the parent hirulog compound used to exemplify the present invention is shown in FIG. 2A (SEQ ID NO:10).

Although exemplified using the parent substances described above, the present invention will also find use with a wide variety of other parent proteins and polypeptide agents, such as other polypeptides derived from eucaryotic, procaryotic and viral sources, as well as synthetic peptides. Such polypeptides will generally have from about 10 to about 50 amino acids, a secondary structure amenable to manipulation and will not be prone to adopt a stable tertiary folded structure, eg, as a result of a high concentration of Cys residues. Such polypeptides include, without limitation, peptide drugs which are antibiotics and antiviral agents, antineoplastics, immunomodulators, peptide hormones such as ACTH, CRF, GHRH, cholecystokinin, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like.

The secondary structure of the parent polypeptide is generally manipulated by replacing one or more selected parent amino acid residues with one or more amino acid residues having a lower tendency to form α-helix and/or β-sheet conformations. In this regard, each amino acid residue demonstrates conformational preferences. One measure of the relative tendency of a particular residue to be involved in an α-helix or β-strand has been defined by the parameters Pα and Pβ (Chou, P. Y. and Fasman, G. D. Ann. Rev. Biochem. (1978) 47:251–276). An updated and revised list of Pα and Pβ values are depicted in Table 1. The Pα values in Table 1 which are greater than 1.00 represent amino acids which favor α-helical conformations and are defined herein as "high Pα values." Similarly, the Pβ values in Table 1 which are greater than 1.00 represent amino acids which favor β-strand formation and are defined herein as "high Pβ values." The amino acids with Pα and Pβ values of 1.00 or less disfavor or break the secondary conformations and are defined herein as "low Pα values" and "low Pβ values," respectively.

Thus, for example, the amino acids Glu, Ala and Leu have high Pα values and favor helix formation, while Pro, Gly, Ser, Cys, Tyr and Asn have low Pα values and therefore disfavor helix formation. Similarly, the amino acid residues Val, Ile and Tyr have high Pβ values and favor B-strand formation, while the amino acids Pro, Asp, Asn, Glu and Gly, disfavor such formation. Combining Pα and Pβ values, the amino acids which should exhibit the lowest tendency to form these types of secondary structures are Gly, Asn, Pro and Ser.

TABLE 1

Conformational Preferences of the Amino Acids

| Amino Acid Residue | α-helix (Pα) | β-strand (Pβ) |
|---|---|---|
| Glu | 1.59 | 0.52 |
| Ala | 1.41 | 0.72 |
| Leu | 1.34 | 1.22 |
| Met | 1.30 | 1.14 |
| Gln | 1.27 | 0.98 |
| Lys | 1.23 | 0.69 |
| Arg | 1.21 | 0.84 |
| His | 1.05 | 0.80 |
| Val | 0.90 | 1.87 |
| Ile | 1.09 | 1.67 |
| Tyr | 0.74 | 1.45 |
| Cys | 0.66 | 1.40 |

TABLE 1-continued

Conformational Preferences of the Amino Acids

| Amino Acid Residue | α-helix (Pα) | β-strand (Pβ) |
|---|---|---|
| Trp | 1.02 | 1.35 |
| Phe | 1.16 | 1.33 |
| Thr | 0.76 | 1.17 |
| Gly | 0.43 | 0.58 |
| Asn | 0.76 | 0.48 |
| Pro | 0.34 | 0.31 |
| Ser | 0.57 | 0.96 |
| Asp | 0.99 | 0.39 |

*Data in Table 1 was taken from T.E. Creighton, Proteins: Structures and Molecular Properties (W. H. Freeman and Company 1993), p 256.

A segment of a particular secondary structure is much more probable when several adjacent residues prefer that structure. Thus, an α-helix can be predicted if four out of six adjacent residues are helix-favoring and if the average Pα value is greater than 1.05 and greater than Pβ. Similarly, a β-strand is predicted if three out of five adjacent residues are sheet-favoring and if the average value of Pβ is greater than 1.04 and greater than Pα. T. E. Creighton, *Proteins: Structures and Molecular Properties* (W.H. Freeman and Company, 1993), pp 255–257.

Thus, using these principles, amino acid residues in portions of the molecule that are prone to α-helix and β-sheet formation, can be replaced with those residues from Table 1 which disfavor such conformations. Preferably, a residue with a high Pα or Pβ value will be replaced with a residue having a low Pα or Pβ value, respectively.

Other methods of determining the propensity of a polypeptide to form α-helical and β-sheet segments are also known. For example, the α-helix potential of a linear polypeptide can be estimated by, eg, the Lifson-Roig equations (S. Lifson and A. Roig *J. Chem. Phys.* (1961) 34:1963–1974) using values for the residue helix formation parameters converted from their calculated Zimm-Bragg values (Zimm, B. H. and Bragg, J. K. *J. Chem. Phys.* (1959) 31:526–535) employing conversion equations of Qian and Schellman (Qian, H. and Schellman, J. A. *J. Chem. Phys.* (1992) 96:3987–3994).

More particularly, the Zimm-Bragg parameters, s and σ, represent the helix-coil stability constant and the nucleation factor, respectively. A set of Zimm-Bragg s and σ values have been defined for each amino acid residue (see Table 1 of Finkelstein et al. *Proteins: Structure, Function and Genetics* (1991) 10:287–299) and the probability that the entire polypeptide chain (or some defined subsequence) would adopt an α-helix may be computed using the reported equations.

The corresponding Lifson-Roig helix parameters, u, v and w, can also be used to make a similar determination (Lifson, S and Roig, A. *J. Chem. Phys.* (1961) 34:1963–1974). In this regard, w, which is used to define a peptide unit at the interior of an uninterrupted sequence of helical states, can be computed from s. Lifson-Roig's v defines a peptide unit at the beginning or t the end of an uninterrupted sequence of helical states and can be computed from the Zimm-Bragg parameter $\sigma^{1/2}$. The factor u, defines the statistical weight of the coil region and does not correspond to a Zimm-Bragg parameter.

Using these parameters, there are two calculations generally used to estimate α-helix potential. The first takes the Lifson-Roig helix initiation parameter v to be a constant 0.039 (ie, the Zimm-Bragg a parameter is 0.0013 for all residues), with the w parameter for each amino acid calculated from the Zimm-Bragg s value found in Table 1 of Finkelstein et al. *Proteins: Structure, Function and Genetics* (1991) 10:287–299. The second computation does not assume that all residues have the same value for the helix initiation parameter v (ie, the Zimm-Bragg σ parameter is unique for each amino acid residue). Using this method, the Zimm-Bragg s and σ values for each residue can be determined from Table 1 of Skolnick, J. and Holtzer, A. *Macromolecules* (1982) 15:812–821. These methods are described further below in the examples.

The polypeptide analogs of the present invention can be produced in any number of ways which are well known in the art. In this regard, since the analogs are relatively small, ie, up to about 50 amino acids in length, they can be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, eg, J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3–254, for solid phase peptide synthesis techniques; and M. Bodansky, *Principles of Peptide Synthesis,* (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptide analogs of the present invention can also be chemically prepared by other methods such as by the method of simultaneous multiple peptide synthesis. See, eg, Houghten *Proc. Natl. Acad. Sci. USA* (1985) 82:5131–5135; U.S. Pat. No. 4,631,211.

Alternatively, the peptides can be produced by recombinant techniques, eg, by synthesizing DNA encoding the desired peptide, along with an ATG initiation codon. The nucleotide sequence can be designed with the appropriate codons for the particular amino acid sequence desired. In general, one selects preferred codons for the intended host in which the sequence is expressed. The complete sequence is generally assembled from overlapping oligonucleotides prepared by standard methods and assembled into a complete coding sequence. See, eg, Edge *Nature* (1981) 292:756; Nambair et al. *Science* (1984) 223:1299; Jay et al. *J. Biol. Chem.* (1984) 259:6311. Automated synthetic techniques such as phosphoramide solid-phase synthesis, can be used to generate the nucleotide sequence. See, eg, Beaucage, S. L. et al. *Tet. Lett.* (1981)22:1859–1862; Matteucci, M. D. et al. *J. Am. Chem. Soc.* (1981) 103.3185–3191. Next the DNA is cloned into an appropriate expression vector, either procaryotic or eucaryotic, using conventional methods.

Alternatively, recombinant techniques are readily used to clone the parent polypeptide gene which can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer which hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, eg, Dalbie-McFarland et al. *Proc. Natl. Acad. Sci USA* (1982) 79:6409.

Using the above methods, a number of representative polypeptide analogs exhibiting enhanced electrotransport flux have been made. In particular, FIG. 1B (SEQ ID NO:7) depicts the sequence of PTH analog 1. This PTH analog differs from the parent sequence (depicted in FIG. 1A) (SEQ ID NO:6) as follows: $Met_8$ has been substituted with Leu; $Leu_{15}$ has been substituted with Arg; $Met_{18}$ has been substituted with Leu; $Glu_{19}$ has been substituted with Arg; $Glu_{22}$ has been substituted with Arg; $Gln_{29}$ has been substituted with Lys; $Phe_{34}$ has been substituted with Tyr; and a homoserine lactone is present at the C-terminus of the peptide.

PTH analog 2, depicted in FIG. 1C (SEQ ID NO:8), differs from the parent sequence (FIG. 1A) (SEQ ID NO:6) as follows: $Met_8$ has been substituted with Leu; $Leu_{11}$ has been substituted with Ser; $Leu_{15}$ has been substituted with Arg; $Leu_{18}$ has been substituted with Ser; $Met_{18}$ has been substituted with Ser; $Glu_{19}$ has been substituted with Arg; $Val_{21}$ has been substituted with Ser; $Glu_{22}$ has been substituted with Arg; $Leu_{24}$ has been substituted with Ser; $Leu_{28}$ has been substituted with Ser; $Gln_{29}$ has been substituted with Lys; $Tyr_{34}$ has been substituted with Ser; and a homoserine lactone is present at the C-terminus of the peptide. Taken together, these substitutions result in a lessened secondary structure.

The hirulogs are a series of synthetic analogs of hirudin, a natural thrombin inhibitor. Two of these analogs are shown in FIG. 2 (SEQ ID NOS:10, 11, 12). Hirulog-1, shown in FIG. 2B (SEQ ID NO:11) is disclosed in Maragnore et al. *Biochem.* (1990) 29:7095–7101. Hirulog-B2, a twenty amino acid peptide with a molecular weight of about 2186 daltons, has the sequence shown in FIG. 2C (SEQ ID NO:12). As can be seen, the hirulog-B2 analog differs from the hirulog-1 analog shown in FIG. 2C (SEQ ID NO:12), in that it has D-cyclohexylalanine substituted for D-phenylalanine in the first position. Hirulog-B2 is described in Witting et al. *Biochem. J.* (1992) 287:663–664; and International Publication No. WO 92/13952.

Once the desired polypeptide analog is prepared, it can be delivered to the subject using any of several electrotransport drug delivery systems and is not limited to the use of one particular system. Examples of electrotransport drug delivery systems are described in, eg, U.S. Pat. Nos. 5,312,326 to Myers et al., 5,080,646 to Theeuwes et al., 5,387,189 to Gyory et al., and 5,169,383 to Gyory et al., the disclosures of which are incorporated by reference herein.

FIG. 3 illustrates a representative electrotransport delivery device that may be used in conjunction with the present method. Device 10 comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10 on a patient's skin. Upper housing 16 is preferably composed of an injection moldable elastomer (eg, ethylene vinyl acetate). Printed circuit board assembly 18 comprises an integrated circuit 19 coupled to discrete components 40 and battery 32. Circuit board assembly 18 is attached to housing 16 by posts (not shown in FIG. 3) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10.

The device 10 is generally comprised of battery 32, electronic circuitry 19,40, electrodes 22,24, and drug/chemical reservoirs 26,28, all of which are integrated into a self-contained unit. The outputs (not shown in FIG. 3) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Device 10 optionally has a feature which allows the patient to is self-administer a dose of drug by electrotransport. Upon depression of push button switch 12, the electronic circuitry on circuit board assembly 18 delivers a predetermined DC current to the electrodes/reservoirs 22,26 and 24,28 for a delivery interval of predetermined length. The push button switch 12 is conveniently located on the top side of device 10 and is easily actuated through clothing. A double press of the push button switch 12 within a short time period, eg, three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible sound signal from, eg, a "beeper". Drug is delivered through the patient's skin by electrotransport, eg, on the arm, over the predetermined delivery interval.

Anodic electrode 22 is preferably comprised of silver and cathodic electrode 24 is preferably comprised of silver chloride. Both reservoirs 26 and 28 are preferably comprised of polymer hydrogel materials. Electrodes 22,24 and reservoirs 26,28 are retained within the depressions 25',25 in lower housing 20.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (eg, polyethylene) which can be easily molded to form depressions 25,25' and cut to form openings 23,23'. The assembled device 10 is preferably water resistant (ie, splash proof) and is most preferably waterproof. The system has a low profile that easily conforms to the body, thereby allowing freedom of movement at, and around, the wearing site. The reservoirs 26 and 28 are located on the skin-contacting side of the device 10 and are sufficiently separated to prevent accidental electrical shorting during normal handling and use.

The device 10 adheres to the patient's body surface (eg, skin) by means of a peripheral adhesive 30 which has upper side 34 and body-contacting side 36. The adhesive side 36 has adhesive properties which assures that the device 10 remains in place on the body during normal user activity, and yet permits reasonable removal after the predetermined (eg, 24-hour) wear period. Upper adhesive side 34 adheres to lower housing 20 and retains lower housing 20 attached to upper housing 16.

The reservoirs 26 and 28 generally comprise a gel matrix, with the drug solution uniformly dispersed in at least one of the reservoirs 26 and 28. Drug concentrations in the range of approximately $1 \times 10^{-4}$ M to 1.0 M or more can be used, with drug concentrations in the lower portion of the range being preferred. Suitable polymers for the gel matrix may comprise essentially any nonionic synthetic and/or naturally occurring polymeric materials. A polar nature is preferred when the active agent is polar and/or capable of ionization, so as to enhance agent solubility. Optionally, the gel matrix will be water swellable. Examples of suitable synthetic polymers include, but are not limited to, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(vinyl alcohol) and poly (allyl alcohol). Hydroxyl functional condensation polymers (ie, polyesters, polycarbonates, polyurethanes) are also examples of suitable polar synthetic polymers. Polar naturally occurring polymers (or derivatives thereof) suitable for use as the gel matrix are exemplified by cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers can also be used for the matrix provided that the available counterions are either drug ions or other ions that are oppositely charged relative to the active agent.

Thus, the polypeptide analogs of the present invention will be incorporated into the drug reservoir, eg, a gel matrix as just described, and administered to a patient using an electrotransport drug delivery system, optionally as exemplified hereinabove. Incorporation of the drug solution can be done any number of ways, ie, by imbibing the solution into the reservoir matrix, by admixing the drug solution with the matrix material prior to hydrogel formation, or the like.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

III. Experimental

In general, standard techniques of recombinant DNA technology are described in various publications, eg, Sambrook, et al., *Molecular Cloning: A Laboratory Manual* (Cold Spring Harbor Laboratory, 1989); Ausubel et al., *Current Protocols in Molecular Biology*, vols. 1 and 2 and supplements (1987); and Wu and Grossman (eds.), *Methods in Enzymology*, Vol. 53 (Recombinant DNA Part D, 1987). Restriction enzymes, mammalian cell culture media, and *E. coli* cell line DH10B (F-mcrA D(mrr-hsdRMS-mcrBC) F80dlacZDM15 DlacX74 deoR recA1 araD139 D(ara,leu) 7697 galU galK I-rpsL endA1 nupG) were purchased from Gibco/BRL (Gaithersburg, Md.). Taq polymerase was from Perkin Elmer Cetus (Norwalk, Conn.). His-bind resin was purchased from Novagen (Madison, Wis.) and used according to the manufacturer's instructions. DNase and lysozyme were purchased from Boehringer Mannheim (Indianapolis, Ind.). Cyanogen bromide was purchased from Aldrich (Milwaukee, Wis.). Oligonucleotides were synthesized on an Applied Biosystems Inc. (Foster City, Calif.), Model 394 DNA synthesizer using ABI chemicals. Synthetic human parathyroid hormone, and synthetic bovine parathyroid hormone were purchased from Bachem (Torrance, Calif.).

EXAMPLE 1

Construction of Expression Vectors for the PTH Polypeptides

The PTH expression vectors were constructed in several steps using plasmid pBAD18 (Guzman et al. 1995) as the starting plasmid. Plasmid pBAD18 contains the araB promoter followed by a polylinker and a terminator under the control of the positive/negative regulator araC, also specified by the plasmid. Plasmid pBAD18 also contains a modified plasmid pBR322 origin and the bla gene to permit replication and selection in *E. coil*, as well as the phage M13 intragenic region to permit rescue of single-stranded DNA. For purposes of the present invention, however, the actual cloning vector used to construct the expression vectors of the invention is not critical.

For instance, plasmid pMC3, could serve as the cloning vector in place of plasmid pBAD18 in the protocols below. Plasmid pMC3 is described in U.S. Pat. No. 5,270,170. Plasmid pMC3 differs from plasmid pBAD18 in that plasmid pMC3 encodes a dynorphin B-tailed lac repressor in the region corresponding to the Nhel-Xbal region of the multiple cloning site of pBAD18 and encodes a lac operator sequence in the region corresponding to the Ndel-Clal fragment of plasmid pBAD18. As this latter fragment is not essential for purposes of the present invention, one could readily construct suitable vectors for purposes of the present invention from plasmid pMC3. Plasmid pMC3 is available in strain ARI161 from the American Type Culture Collection under the accession number ATCC 68818.

The PTH vectors were then constructed as follows. The following pair of partially overlapping oligonucleotides were annealed and second strand synthesis was performed with Taq polymerase:

```
5'-GCTCGGGCTAGC TAA CTA ATGGAGGAT ACA TAA ATGAAAGCTATCTTC
         Nhe I            S&D              TrpLe leader GTTCTGAAAGGTTCCCTG GAC CGT GAC CCG GA-3'
              3'-ACCTGGCACTGGGCCTTAAG CAGCTG TACTAG
                                      Sal I    Bcl I TTG GTCTAGAGG GTGGTGGTGGTAGTGGTA ATT ATT TTCGAA GGC AGG-5'      (SEQ ID NO:4, SEQ ID NO:3, and
                                                                 SEQ ID NO:5)
     Bgl II        His6                  Hind III
PS
```

The product was digested with NheI and HinDIII and inserted into the corresponding sites of pBAD18. The duplex contains the Shine-Dalgarno ribosome binding site (S&D) and the TrpLE leader peptide. This 17 amino acid leader sequence has been previously shown to enhance expression of small proteins and may promote the sequestering of fusions into inclusion bodies (Derynck et al. *Cell* (1984) 38:287–297; Miozzari and Yanofsky *J. Bacteriol.* (1978) 133:1457–1466). The TrpLe leader peptide is separated from the $His_6$ sequence by a multiple cloning site. The polyhistidine site allows for rapid purification of the recombinant parathyroid hormone molecule (RPTH), and RPTH analogs via nickel chelation chromatography (see U.S. Pat. No. 4,551,271). Two stop codons (TAATAA) follow the polyhistidine.

An RPTH(1-34) gene with the following sequence was designed and synthesized using high-use *E. coli* codons:

```
                                         1   2   3  1 4   5   6   7   8
              Val-Asp-Met-Ile-Asn-Met-Ser-Val-Ser-Glu-Ile-Gln-Leu-Leu
5'-GGC TGG GTCGAC ATG ATC AAC ATG TCC GTT TCC GAA ATC CAG CTG CTG
3'-CCG ACC CAGCTG TAC TAG TTG TAC AGG CAA AGG CTT TAG GTC GAC GAC
           Sal I 9   10  11  12  13  14  15  16  17  18  19  20  21  22  23  24
His-Asn-Leu-Gly Lys-His-Leu-Asn-Ser-Leu-Glu-Arg-Val-Glu-Trp-Leu
CAC AAC CTG GGT AAA CAC CTG AAC TCC CTC GAG CGT GTT GAA TGG CTG
GTG TTG GAC CCA TTT GTG GAC TTG AGG GAG CTC GCA CAA CTT ACC GAC 25  26  27  28  29  30  31  32  33  34
Arg-Lys-Lys-Leu-Gln-Asp-Val-His-Asn-Tyr-Met-Gln-Ile-Ser
CGT AAA AAA CTG CAG GAC GTC CAC AAC TAC ATG CAGATCTCC CTC-3'
GCA TTT TTT GAC GTC CTG CAG GTG TTG ATG TAC GTCTAGAGG GAG-5'             (SEQ ID NO:4, SEQ
                                                                         ID NO:3, and SEQ
                                                                         ID NO:5)
                                         BgI II
```

This RPTH gene was digested with SalI and BglII and inserted into the modified pBAD vector.

EXAMPLE 2

Expression and Purification of PTH Polypeptides

*E. coli* DH10B containing the plasmid described above was grown overnight in LB-media containing ampicillin (50 to 100 µg/mL). Ten mL of this culture were used to inoculate a 500 mL culture of Superbroth (35 g/L Bactotryptone, 20 g/L yeast extract, 5 g/L NaCl, and NaOH to pH=7.5) containing ampicillin. The cells were allowed to grow to an $OD_{600}$ of about 0.5 to 1.0 and L-(+)-arabinose was added to a final concentration of 0.2%. The cells were allowed to grow for an additional 3 hours. At the end of this time, the $OD_{600}$ was between 1.5 to 3. The cells were harvested by centrifugation and washed sequentially with 250 mL of WTEK buffer (50 mM Tris, pH=7.5, 10 mM EDTA, 100 mM KCl); 250 mL of PBS; and 250 mL of 10 mM Tris, pH=7.5. The cells were then resuspended in 100 mL of a solution composed of 10 mM Tris, pH=7.5; 0.1 mg/mL of protease inhibitor N-tosyl-L-phenylalanine chloromethyl ketone (TPCK); 0.1 mg/mL of protease inhibitor N-tosyl-L-lysine chloromethyl ketone (TLCK); 0.1 mg/mL of protease inhibitor phenylmethylsulfonyl fluoride (PMSF); and 0.05 mgimL lysozyme). The resulting solution was incubated on ice for 1 hour. The cells were then freezethawed; 1 mg of DNAse was added to the freeze-thawed cells; and the resulting mixture was incubated on ice for an additional hour.

Inclusion bodies from the cells were purified by centrifugation at 10,000×g for 15 minutes. The inclusion bodies were solubilized in 10% SDS, but in some cases, sonication of the sample was also necessary to solubilize all of the protein. Binding buffer (5 mM imidazole, 500 mM NaCl, and 20 mM Tris, pH=7.9) was added to dilute the SDS concentration to 1%, and the sample was loaded onto a column containing His-bind resin (Novagen). The column was then washed with 15 column volumes of binding buffer, and bound protein was then eluted with 1 column volume of elution buffer (500 mM NaCl, 100 mM EDTA, and 50 mM Tris, pH=7.9). Two volumes of absolute ethanol were then added to precipitate the protein.

The precipitated PTH polymer was then dissolved in 70% formic acid, and a 500-fold (100 to 1000-fold excess can be used) molar excess of CNBr was added. A time course of cleavage (conducted at different CNBr concentrations to determine the optimal time), as assayed by amino acid analysis, indicated that complete cleavage was achieved in 2 hours at room temperature. After CNBr cleavage, the peptides were lyophilized and resuspended in distilled water.

The peptide was resuspended in Buffer A (0.1% TFA) and further purified by HPLC using a VYDAC C-18 semi-preparative column. Approximately 30 mg of peptide was injected onto the column. The peptide was then eluted with a gradient of 20–40% acetonitrile/0.1% TFA over 40 minutes. The major peak, eluting at approximately 15 minutes, was collected and lyophilized to dryness.

After isolation of inclusion bodies and purification as described above, the peptide was greater than 95% pure as determined by SDS-PAGE. The peptide was then desalted and partially purified on a SepPak column. Individual peaks were isolated and analyzed by electrospray mass spectrometry to determine the composition. Two minor peaks were present which were the result of incomplete cyanogen bromide cleavage and represented the PTH-His$_6$ peptide and the I-N-M-PTH peptide. The major peak comprised greater than 80% of the total protein. Comparison of the "crude" Sep-Pak purfied sample with an HPLC purified RPTH showed no significant difference in adenylate cyclase stimulatory ability.

EXAMPLE 3

Production of PTH Analogs

In order to produce the PTH analogs of the present invention, the PTH peptide was substituted with the amino acids indicated in FIGS. 1B, 1C and 1D (SEQ ID NOS:7, 8, 9). PTH analogs were recombinantly produced constructed in a manner similar to that described above for the recombinant RPTH-A gene by substituting the appropriate bases. The PTH analogs were expressed and purified as described above.

EXAMPLE 4

PTH Analog Activity Assay

Synthetic PTH having the wild-type sequence and the recombinant PTH (RPTH) analogs were assayed for their ability to stimulate adenylate cyclase. PTH concentrations were determined by OD$_{280}$ using an extinction coefficient of 6600 for the recombinant peptide and 5500 for the synthetic peptide. The rat osteosarcoma cell line UMR106 (ATCC CRL 1661) was used for in vitro testing of the peptide's ability to activate the PTH receptor. Activation of the PTH receptor leads to an intracellular rise in cAMP concentration.

The UMR106 cells were seeded at about $2.5 \times 10^5$ per well in a 48 well dish and allowed to grow to confluence. Assays were performed on cells 3–5 days postconfluence. The media (Dulbecco's modified Eagle's medium, DMEM, with fetal calf serum) was removed, and 1 mL of fresh media was applied. PTH (recombinant or synthetic) at various concentrations and 3-isobutyl-1-methyl xanthine (IBMX) at 1 mM final concentration were then added to each well of the plate, which was then incubated for 5 minutes at room temperature. The media was then removed and the cells quickly washed with ice cold PBS. The cells were then extracted twice with 1 mL of absolute ethanol. The two extractions were combined and the ethanol removed by evaporation. The extract was then redissolved in 1 mL of scintillation proximity buffer (SPA buffer) (Amersham, Arlington Heights, Ill.). The cAMP concentration was determined by assay using a scintillation proximity assay (SPA) kit available from Amersham. Analog 1 had a Kd (dissociation constant) of 1.5 nM and an EC-50 (effective concentration) of 0.9 nM. Wild-type PTH had a Kd of 8.5 nM and an EC-50 of 4.4 nM. Analogs 2 and 3 have no measurable activity.

EXAMPLE 5

Prediction of the Effects of Amino Acid Substitutions in the PTH Analogs on α-Helix Potential As explained above, the α-helix potential of linear polypeptides can be estimated using the Lifson-Roig equations (Lifson, S and Roig, A. *J. Chem. Phys.* (1961 ) 34:1963–1974) and values for the residue helix formation parameters converted from their Zimm-Bragg values (Zimm, B. H. and Bragg, J. K. *J. Chem. Phys.* (1959) 31:526–535), employing conversion equations of Qian and Schellman (Qian, H. and Schellman, J. A. *J. Chem. Phys.* (1992) 96:3987–3994). Once a set of Zimm-Bragg s and σ values are defined for each residue, then the probability that the entire polypeptide chain (or some defined subsequence) adopts an α-helix may be computed using equations in the above references.

The two calculations generally used to estimate α-helix potential, described above, were applied to the two PTH analogs generated. The first calculation takes the Lifson-Roig helix initiation parameter v to be a constant 0.039 (ie, the Zimm Bragg σ parameter is 0.0013 for all residues), with the w parameter for each amino acid calculated from the Zimm-Bragg s value found in Table 1 of Finkelstein et al. (Finkelstein et al. *Proteins: Structure, Function and Genetics* (1991) 10:287–299). In applying the calculations to the PTH analogs, the s values in Table 1 of this reference were first converted from their 300° K values to the estimated values at 273° K using an assumed enthalpy change of 1 kcal/mol (identical for all residues). For PTH analog 1 this calculation gives a probability of 0.41 that the entire sequence is α-helical. For PTH analog 2 this calculation gives a probability of 0.18 that the entire sequence is α-helical. For PTH analog 3 this calculation gives a probability of 0.15 that the entire sequence is α-helical.

The second computation does not assume that all residues have the same value for the helix initiation parameter v (ie, the Zimm-Bragg σ parameter is unique for each amino acid residue). In this case the Zimm-Bragg s and σ values for each residue were taken (except for His, Pro, and Trp) from Table 1 of Skolnick, J. and Holtzer, A *Macromolecules* (1982) 15:812–821. The Zimm-Bragg values for His were taken from Sueki et al. *Macromolecules* (1984) 17:148–155. The Zimm-Bragg values for Pro and Trp were taken from Finkelstein et al. For this second alternative calculation in every case the s value was computed at 273° K, and for the residues having ionizable side chains, the s value for the state of ionization which would predominate at pH 7 was assumed. The s values (at 273° K) and σ values obtained from Sueki et al. and Skolnick and Holtzer were converted (Qian and Schellman) to their Lifson-Roig v and w values and then used to compute the probability that the entire polypeptide chain (or some subsequence) exists in the α-helical state. For PTH analog 1 this calculation gives a probability of 0.07 that the entire sequence is α-helical. For PTH analog 2 this calculation gives a probability of 0.02 that the entire sequence is α-helical. For PTH analog 3 this calculation gives a probability of 0.02 that the entire sequence is α-helical.

Taken together both sets of assumptions regarding the tendency of polypeptides to assume an α-helical conformation predicts that analog 1 should be two to three times more likely to exist as an α-helix as analog 2.

EXAMPLE 6

Estimating α-Helical Potential from Circular Dichroism in Varying Trifluoroethanol Concentrations The trifluoroethanol (TFE) circular dichroism studies were done using an AVIV Associates, Inc. Model 62DS Circular Dichroism Spectrometer. Protein concentrations were determined from absorbance readings using calculated extinction coefficients for the analogs in 10 mM ionic buffer. TFE titrations were done from 0 to 50% TFE, scanning from 250 to 200 nm at 20° C. for each TFE sample. $[\theta]_{222}$ was calculated from: $\theta_{observed\ at\ 222}$*(mean residue weight)/(10 (cell path length)(protein concentration)).

Data from the TFE titrations at pH 6.5 10 mM cacodylate are summarized below in Table 2 for the PTH analogs and plotted in FIG. 4. FIG. 4 demonstrates that when the α-helix inducing cosolvent, trifluoroethanol reaches 30% (v/v) concentration that essentially the maximum amount of helix is formed for both PTH and analog 1, with the average amount of helicity being about 80%. The parent PTH, even in the absence of the helix-inducing agent, is about 20% α-helical.

PTH analog 2 in the absence of the helix-inducing TFE is essentially devoid of helix, and at 30% TFE is at most about 30% α-helical.

PTH analog 3 in the absence of the helix-inducing TFE is essentially devoid of helix, and at 30% TFE is about 15% α-helical.

This 2–3 fold reduction in the observed helical content at 30% trifluoroethanol was predictable based on the Lifson-Roig equation, and calculations derived from it as referred to above.

TABLE 2

TFE TITRATION DATA

| % TFE | $[\ ]_{222}$ for hPTH(1–34) | $[\ ]_{222}$ for analog 1 | $[\ ]_{222}$ for analog 2 | $[\ ]_{222}$ for analog 3 |
| --- | --- | --- | --- | --- |
| 0  | −7793  | −4205  | −2750  | −3867  |
| 10 | −15863 | −9333  | −4600  | −6479  |
| 20 | −21491 | −23098 | −9065  | −12329 |
| 30 | −26288 | −26334 | −12081 | −15161 |
| 40 | −27011 | −27580 | −14320 | −15191 |
| 50 | −26802 | −27705 | −15649 | −15395 |

EXAMPLE 7

In Vitro Electrotransport Flux of the PTH Analogs

In vitro electrotransport studies were carried out in multi-compartment, custom-built, small volume cells using anodic drive. 1 mM PTH in 10 mM buffer was placed in the donor compartment and 25 mM final ionic strength receptor was placed in the receptor compartment. The receptor solution for the native PTH and analogs 1 and 2 was 15 mM NaCl buffered to pH 7 with 10 mM imidazole, 0.1% bovine serum albumin (BSA) as a blocking agent, Tween 20 detergent and sodium azide as a bactericide. The receptor solution for the PTH analog 3 was 15 mM NaCl buffered to pH 7 with 10 mM imidizole, 0.5% dodecyltrimethyl ammonium bromide (DTAB, a surfactant) and 0.3 mg/mL Trp-Nle-Arg-Phe-amide, a tetrapeptide used as an "alternate" substrate for proteolytic enzymes present in the skin.

Heat-stripped human cadaver stratum corneum was placed between the donor and receptor compartments with the epidermis side toward the receptor compartment. A constant DC current of 127 $\mu$A mA (ie, 0.1 mA/cm$^2$) was applied. Cells were maintained at 32° C. during the in vitro studies with receptor samples taken every 2 hours (receptor volume removed and replaced with "fresh" receptor at each sampling). Receptor samples were analyzed by reversed-phase HPLC.

Peak areas of PTH receptor samples were compared to standard curves of the same analog of known concentrations run at the same time using an analytical polymeric column, at a flow rate of 1.5 mL/min with a gradient from 10–50% B in ten minutes for elution. Buffer A was 0.1% trifluroacetic acid (TFA), 1% acetonitrile; Buffer B was 0.1% TFA, 98.9% acetonitrile. Analog concentrations were converted to mass flux and plotted vs. time.

For the in vitro electrotransport studies, described donors contained the retro-inverso versions (ie, D-amino acid residues were used and were assembled in reverse order than usual) of the PTH analogs 1 and 2 (1 mM) in aqueous solutions at pH 5.0. This was because PTH analogs 1 and 2 were not stable when incubated with stripped stratum corneum, probably due to proteolytic digestion by skin proteases. PTH analog 3 was not a retro-inverso version, but instead was recombinantly synthesized. In order to protect analog 3 from proteolytic enzyme digestion, the tetrapeptide was added to the receptor solution. The fully assembled electrotransport cells were incubated at 32±0.5° C. The skin contact area available for transport was 1.27 cm$^2$. The donor compartment volume was 200 $\mu$L; the receptor compartment volume was 350 $\mu$L. The receptor solution was separated from the cathode by an anion exchange membrane (Ionac™, Eletrosynthesis Co., Lancaster, N.Y.). Each cell was connected to a constant current source at a standard current density of 100 $\mu$A cm$^{-2}$. The voltage drop across each cell was monitored at approximately 2-hour intervals for the duration of the experiment.

Histograms of mass flux for each time point were plotted. The median mass flux (95% confidence interval) for PTH analog 1 was 0.3 $\mu$g cm$^{-2}$h$^{-1}$ (0.1 to 0.7), for PTH analog 2 was 3.2 $\mu$g cm$^{-2}$h$^{-1}$ (2.1 to 4.2) and for PTH analog 3 was 1.1 $\mu$g cm$^{-2}$ h$^{-1}$ (0.9–1.7). Average mass flux values±sd for these analogs were 1.4 $\mu$g cm$^{-2}$h$^{-1}$±2.3; 4.1 $\mu$g cm$^{-2}$h$^{-1}$±3.7; and 1.5 $\mu$g cm$^{-2}$ h$^{-1}$±1.1 for analogs 1, 2 and 3, respectively.

EXAMPLE 8

Estimating α-Helical Potential from Circular Dichroism in Varying Trifluoroethanol Concentrations The trifluoroethanol (TFE) circular dichroism studies were done using an AVIV Associates, Inc. Model 62DS Circular Dichroism Spectrometer. Protein concentrations were determined from absorbance readings using calculated extinction coefficients for the analogs in 10 mM ionic buffer. TFE titrations were done from 0 to 50% TFE, scanning from 250 to 200 nm at 20° C. for each TFE sample. $[\theta]_{222}$ was calculated from: $\theta_{observed\ at\ 222}$*(mean residue weight)/(10 (cell path length)(protein concentration)).

Data from the TFE titrations at pH 6.5 10 mM cacodylate are summarized below in Table 3 for the hirulog analogs and plotted in FIG. 5. FIG. 5 demonstrates that when the α-helix inducing cosolvent, trifluoroethanol reaches 30% (v/v) concentration that essentially the maximum amount of helix is formed for both the parent hirulog and analog B2, with the average amount of helicity being about 10% for the parent hirulog and essentially 0% for the analog B2. The parent hirulog and the analog B2 exhibit no α-helicity in the absence of the helix-inducing TFE. The hirulog-B2 analog had essentially no α-helix even at 80% TFE concentrations.

TABLE 3

TFE TITRATION DATA

| % TFE | [ ]₂₂₂ for hirulog parent | [ ]₂₂₂ for analog B2 |
|---|---|---|
| 0 | −1120 | −989 |
| 10 | −3679 | −1313 |
| 20 | −5458 | −1580 |
| 30 | −6972 | −1848 |
| 40 | −8365 | −1896 |
| 50 | −8493 | −1963 |

EXAMPLE 9

In Vitro Electrotransport Flux of Hirulog-B2

Hirulog-B2 was synthesized using standard techniques. See, eg, Maraganore et al. *Thromb. Haemostasis.* (1991) 65:830; Bode et al. *EMBO J.* (1989) 8:3467–3475; and International Publication No. WO 92/13952. The transdermal electrotransport flux of hirulog-B2 was evaluated using heat-seperated human epidermis. In addition, hydrogel formulations were also investigated using human epidermis as was the effect of current density on transdermal drug flux Transdermal hirulog-B2 flux was assessed using aqueous solutions prepared with both as received and desalted drug buffered with 10 mM ionic strength acetate buffer, pH 5. The hirulog-B2 flux studies were performed at a current density of 0.1 mA/cm². Using acetate buffered 15 mM NaCl at pH 5 as the receptor solution, steady-state electrotransport flux of about 19 μg h⁻¹ cm⁻² and 17 μg h⁻¹ cm⁻² were obtained for the desalted and as received drug solutions respectively.

The variability in hirulog-B2 flux for skin samples from a single donor as well as multiple donors appeared to be about 15 to 40%, which is well within the variability ranges observed for peptides and protein compounds.

For the hydrogel studies, hydrogel discs were imbibed with drug and assembled into foam housings. Either as received (11 mM hirulog-B2 in 20 mM acetate) or desalted drug (4 mM hirulog-B2 in 4 mM acetate) solutions were imbibed into gels. An average steady-state electrotransport flux of about 27 μg h⁻¹ cm⁻² was obtained with hydrogel formulations containing either as received or desalted drug.

Using hydrogels imbibed with as received drug, another experiment was undertaken to evaluate the effect of current density on transdermal hirulog-B2 flux. An increase in current density resulted in a corresponding increase in hirulog-B2 flux over the range of current densities examined. Under passive conditions (zero current), no measurable hirulog-B2 flux was observed.

EXAMPLE 10

In Vivo Electrotransport Flux of Hirulog-B2

A. Intravenous Administration of Hirulog-B2

Pigs used for intravenous (IV) studies weighed 11±1 kg (n=3), and were fasted overnight before the bolus injections. IV bolus injections were given in the auricle vein or the vena cava. The IV injection was administered over about 30 to 60 seconds and the dose was about 0.3 mg/kg (in 0.5 mL). Plasma hirulog-B2 levels increased rapidly in all pigs after the IV bolus injection of hirulog-B2, reaching an average peak level of 66±6 ng/mL at the 15 minutes sampling point. Plasma hirulog-B2 levels declined to below 2 ng/mL by 2 hours after the bolus injection, and remained relatively constant from 2 to 8 hours after the bolus injection. The elimination half-life and clearance calculated for each pig are shown in Table 3. The apparent volume of distribution and average elimination half-life were calculated from the IV bolus data as 45.4 L and 16 minutes, respectively.

TABLE 4

PHARMACOKINETICS OF HIRULOG-B2 IN SWINE

| Definitive Phase | Pig 303 | Pig 304 | Pig 305 | Mean | SD |
|---|---|---|---|---|---|
| IV | | | | | |
| BW [kg] | 12 | 11 | 10 | 11 | 1 |
| Ke [1/h] | 2.42 | 2.01 | 2.5 | 2.31 | 0.26 |
| V [L] | 45.5 | 49.25 | 41.55 | 45.43 | 3.85 |
| V [L/Kg] | 3.8 | 45 | 4.2 | 4.2 | 0.35 |
| CL [L/h] | 110 | 99 | 104 | 104 | 5.5 |
| CL [L/h/Kg] | 9.2 | 9.0 | 10.4 | 9.5 | 0.76 |
| Elimination T½ [min] | 17.2 | 20.72 | 16.6 | 18.2[a] | 2.23[a] |
| Sc | | | | 16[b] | — |
| Elimination T½ [min] | — | — | — | 58[b] | — |
| 4-ETS Elimination T½ [min] | — | — | — | 28[b] | — |
| Accumulation T½ [min] | — | — | — | 38[b] | — |

| Screening Phase | Pig SC-3A |
|---|---|
| 3-ETS Elimination T½ [min] | 32 |
| Accumulation T½ [min] | 33 |

[a]Mean calcutated from individual T½ determinations.
[b]Calculated from linear regression of mean hirulog-B2 plasma concentratian vs time curve.

B. Subcutaneous Administration of Hirulog-B2

Pigs were fasted overnight before the subcutaneous (SC) injections. About 0.5 mg/kg (in 0.5 mL) hirulog-B2 was administered SC over a minute. Plasma hirulog-B2 levels peaked within the first hour after injection at 57±10 ng/mL and declined thereafter. The average elimination half-life following SC injection was 58 minutes (Table 4). The plasma hirulog-B2 levels were at about 2 ng/mL by 6 hours following the SC injection, and were relatively constant from 6 to 8 hours.

C. Electrotransport of Hirulog-B2

The electrotransport systems used for hirulog-B2 delivery in vivo included a disposable drug-containing unit in electrical contact with a reusable current controller. The disposable drug-containing unit consisted of a laminated, medical grade, polyethylene adhesive foam tape, housing both the silver foil anodic counter electrode and a cathodic AgCl-loaded polyisobutylene film electrode, and the respective gels. The anode gel made contact with the silver foil anode. A cathodic interface gel made contact with the AgCl cathodic electrode. The interface gel was separated from the drug-containing donor gel by a cation exchange membrane. The donor gel was placed into the cathode cavity of the gel housing just prior to system application.

The drug gels were imbibed the day before electrotransport with hirulog-B2 in acetate buffer (10 mM, pH 5) to give a final concentration of 5 mM peptide. The skin contact area for each drug gel was 6 cm². The applied current density was 0.1 mA/cm².

The electrotransport systems were monitored for current and voltage during electrotransport to confirm electrical continuity of the system. Voltage values were typical for this animal model and indicated an initial decrease followed by fairly constant values over the study duration. The average elimination half-life following termination of electrotransport was 28 minutes (Table 5). The average accumulation half-life at the initiation of electrotransport was 38 minutes. Plasma hirulog-B2 levels peaked after 4 hours of continuous electrotransport at 23±6 ng/mL. The plasma hirulog-B2 levels remained relatively stable, at 21±7 ng/mL, from 2 to 6 hours of electrotransport, and decreased slightly by 8 hours. The apparent decrease in plasma hirulog-B2 levels from 6 to 8 hours of electrotransport may be due to hirulog-B2 depletion in the donor hydrogel. A rapid decrease in plasma hirulog-B2 levels occurred after terminating electrotransport. By 2 hours after terminating electrotransport, the hirulog-B2 plasma levels were at or near 2 ng/mL.

The average elimination from three electrotransport systems following termination of electrotransport was 32 minutes while the average accumulation half-life at the initiation of electrotransport was 33 minutes (Table 5). The plasma hirulog-B2 level peaked after 2 hours of electrotransport at 9 ng/mL after which there was a slow decline in plasma hirulog-B2 levels.

The transdermal flux rates, calculated as both an input rate ($\mu$g/h) and a per unit area flux ($\mu$g/cm$^2$), were calculated using both one-compartment and non-compartmental analyses. The non-compartmental analysis calculates the transdermal drug flux from the concentration of drug in the blood of the animal, which concentration is measured using standard techniques, and the known rate at which the particular drug is cleared from the blood. The one-compartment analysis calculates the transdermal drug flux from the (ie, measured) concentration of drug in the blood of the animal, and the assumption that the animal's absorption of drug administered by IV delivery at any particular rate is the same as that achieved through electrotransport administration, in order to achieve a particular concentration of drug in the blood. The one-compartment and non-compartmental models are discussed in Pharmacokinetics, M. Gibaldi, 2d ed, Marcel Dekker (1982) pps 1–5 and 319–322. The transdermal input and per unit area fluxes using both analyses are shown in Table 4. The average input rate was calculated to be 1873±444 $\mu$g/h, and the flux was calculated to be 78±18 $\mu$g h$^{-1}$ cm$^{-2}$ for four ETS (hirulog-B2) systems using the one compartment model. Using non-compartmental analysis, the input rate was calculated as 1900±523 $\mu$g/h, and the flux was calculated as 79±22 $\mu$g h$^{-1}$ cm$^{-2}$ for four ETS (hirulog-B2) systems. An average flux of 22 $\mu$g h$^{-1}$ cm$^{-2}$ was calculated for the animal in the Screening phase 2 which received three ETS (hirulog-B2) systems.

TABLE 5

CALCULATED ELECTROTRANSPORT INPUT RATES AND FLUX FOR HIRULOG-B2 IN SWINE

| Definitive Phase | Pig 303 | Pig 304 | Pig 305 | Mean | SD |
|---|---|---|---|---|---|
| 4-ETS (one-compartment) | | | | | |
| $K_a$ [1/h] | 3.64 | 2.5 | 2.94 | 3.03 | 0.58 |
| Rate [$\mu$g/h] | 1361 | 2096 | 2161 | 1573 | 444 |
| Flux [$\mu$g/cm$^2$h] | 56.7 | 87.3 | 90.0 | 78.0 | 18.5 |
| 4-ETS (non-compartmental) | | | | | |
| Rate [$\mu$g/h] | 1396 | 1866 | 2440 | 1900 | 523 |
| Flux [$\mu$g/cm$^2$h] | 58.2 | 77.8 | 101.7 | 79.2 | 21.8 |
| Screening Phase | Pig SC-3A | | | | |
| 3-ETS (one-compartment) | | | | | |
| $K_a$ [1/h] | 3.15 | | | | |
| Rate [$\mu$g/h] | 392 | | | | |
| Flux [$\mu$g/cm$^2$h] | 21.8 | | | | |
| 3-ETS (non-compartmental) | | | | | |
| Rate [$\mu$g/h] | 412 | | | | |
| Flux $\mu$g/cm$^2$h] | 22.9 | | | | |

What is claimed is:

1. A method of making an electrotransport device for delivering a polypeptide agent through a body surface by electrotransport, said method comprising:
   (a) providing a first electrode;
   (b) providing a second electrode;
   (c) providing a power source electrically connected to said first and said second electrodes;
   (d) providing at least one donor reservoir associated with an electrode; and
   (e) providing a therapeutically effective amount of the polypeptide agent wherein the polypeptide agent is an analog of a parent polypeptide wherein said parent polypeptide comprises an α-helix and/or a β-sheet segment, the analog polypeptide having one or more amino acid residues substituted relative to said parent polypeptide with an amino acid residue selected from the group consisting of Pro, Gly and Asn to disrupt said α-helical and/or β-sheet segment; and
   (f) adding said polypeptide agent to said donor reservoir to result in an electrotransport device for delivering said polypeptide agent through said body surface.

2. The method of claim 1, wherein said parent polypeptide is hirulog as depicted in FIG. 2A (SEQ ID NO:10).

3. The method of claim 2, wherein said polypeptide analog is hirulog-B2 as depicted in FIG. 2C (SEQ ID NO:12).

4. The method of claim 1, wherein said parent polypeptide is parathyroid hormone (PTH) as depicted in FIG. 1A (SEQ ID NO:6).

5. The method of claim 1, wherein said analog is selected from the group consisting of a PTH analog as depicted in FIG. 1C (SEQ ID NO:8) and FIG. 1D (SEQ ID NO:9).

* * * * *